(12) United States Patent
Barney et al.

(10) Patent No.: US 8,956,874 B2
(45) Date of Patent: Feb. 17, 2015

(54) METHODS FOR EVALUATING CORROSIVITY OF CRUDE OIL FEEDSTOCKS

(75) Inventors: Monica Michele Barney, San Francisco, CA (US); Toni Zhang Miao, Orinda, CA (US); Michael Tung-hai Cheng, Berkeley, CA (US); Grzegorz Jan Kusinski, Moraga, CA (US)

(73) Assignee: Chevron U.S.A. Inc., San Ramon, CA (US)

( * ) Notice: Subject to any disclaimer, the term of this patent is extended or adjusted under 35 U.S.C. 154(b) by 230 days.

(21) Appl. No.: 13/458,166

(22) Filed: Apr. 27, 2012

(65) Prior Publication Data

US 2013/0289320 A1  Oct. 31, 2013

(51) Int. Cl.
*G01N 31/00* (2006.01)
*G01N 31/22* (2006.01)
*G01N 33/28* (2006.01)

(52) U.S. Cl.
USPC ............. 436/6; 208/14; 702/25; 702/30

(58) Field of Classification Search
CPC ..... G01N 33/2876; G01N 31/00; G01N 31/22
USPC ........................................... 436/6
See application file for complete search history.

(56) References Cited

U.S. PATENT DOCUMENTS

| | | | |
|---|---|---|---|
| 2,679,752 A | 6/1954 | Metler | |
| 4,238,298 A | 12/1980 | Tsuru et al. | |
| 4,808,538 A | 2/1989 | Roffey et al. | |
| 5,630,964 A | 5/1997 | Babaian-Kibala et al. | |
| 6,294,387 B1 | 9/2001 | Yepez et al. | |
| 7,723,115 B2* | 5/2010 | Qian et al. | 436/60 |
| 7,983,851 B2* | 7/2011 | Jensen | 702/25 |
| 8,118,994 B2* | 2/2012 | Messer et al. | 208/47 |
| 8,222,605 B2* | 7/2012 | Da Silva et al. | 250/339.08 |
| 2008/0199963 A1* | 8/2008 | Smith et al. | 436/61 |
| 2008/0260584 A1* | 10/2008 | Gudde et al. | 422/69 |
| 2011/0259798 A1* | 10/2011 | Chia et al. | 208/263 |
| 2012/0160707 A1* | 6/2012 | Kusinski et al. | 205/775 |
| 2012/0166099 A1* | 6/2012 | Kusinski et al. | 702/25 |

OTHER PUBLICATIONS

Loahardjo, Improved Oil Recovery, Jan. 18, 2011, Enhanced Oil Recovery Institute, University of Wyoming, pp. 1-66.
Yepez, On the chemical reaction between carboxylic acids and iron, including the special case of naphthenic acid, Science Direct, Elsevier Ltd., St. John's Newfoundland, Canada, 2006, pp. 1-7, at www.sciencedirect.com.
Hau, et al., Measuring naphthenic acid corrosion potential with the Fe powder test, 2003, Rev. Metal Madrid Vo. Extr., pp. 116-123, at http://revistademetalurgia.revistas.csic.es.
Yepez, Influence of different sulfur compounds on corrosion due to naphthenic acid, 2005, Science Direct, Elsevier Ltd., St. John's Newfoundland, Canada, 2005, pp. 1-8, at www.sciencedirect.com.

\* cited by examiner

*Primary Examiner* — Ellen McAvoy
(74) *Attorney, Agent, or Firm* — Melissa Patangia

(57) ABSTRACT

A method for determining corrosiveness of naphthenic acid in a crude oil feedstock is provided. The method includes the steps of providing a crude oil feedstock containing naphthenic acid; contacting the crude oil feedstock with iron for a period of time at a sufficient temperature for the iron to react with the naphthenic acid, forming iron salts. Under sufficiently high temperatures, at least a portion of the iron salts decompose to form ketone, which can be quantified. Measurements of the ketone can be used to correlate with the amount of iron lost from corrosion given a certain level of naphthenic acid present, giving a measure of the corrosivity of crude oil feedstock.

23 Claims, 1 Drawing Sheet

METHODS FOR EVALUATING CORROSIVITY OF CRUDE OIL FEEDSTOCKS

CROSS-REFERENCE TO RELATED APPLICATIONS

None

TECHNICAL FIELD

The invention relates generally to methods for evaluating corrosivity of crude oils and refinery feedstocks, and characterizing the feedstocks according to their corrosivity.

BACKGROUND

Numerous methods have been disclosed to characterize and treat crude oils or refinery feedstocks. Crude oil feedstocks typically contain organic acids such as carboxylic or naphthenic or mineral acids such as hydrochloric, phosphoric, hydrogen sulfide and various oxidized forms of hydrogen sulfide such as sulfuric acid. Evaluation of corrosivity of refinery feedstocks has typically been done by measuring the Total Acid Number (TAN). TAN is computed based on milligrams of KOH required to neutralize one gram sample of the crude.

U.S. Pat. No. 6,294,387 discloses a method for determining corrosiveness of crude oil containing naphthenic acid by measuring the iron content in the crude oil, so as to provide a measure of the extent of corrosion from the naphthenic acids over a period of time.

There is still a need for improved methods to evaluate the corrosivity of crude oil feedstocks, particularly under harsh operating conditions of high temperatures where the iron content in the oil is an unreliable measure of the extent of corrosion. There is also a need to characterize crude oil feedstocks by their corrosivity characteristics.

SUMMARY OF THE INVENTION

In one aspect, a method for evaluating the corrosivity of a crude oil is disclosed. The method comprises: providing a crude oil feedstock containing naphthenic acid; providing an iron sample; contacting a mixture of the iron sample and the crude oil feedstock for a period of time at a sufficiently high temperature to react a portion of the iron sample with the naphthenic acid; and measuring concentration of ketone in the mixture; and correlating the concentration of ketone to the corrosivity of the feedstock. In one embodiment, iron salt concentration is also measured, as the iron sample reacts with the naphthenic acid forming the iron salts at relatively lower temperatures, which subsequently decomposes forming the ketone at higher temperatures.

In another aspect, a method for evaluating corrosivity a crude feedstock is provided. The method comprises: providing a crude oil feedstock containing naphthenic acid; providing an iron sample comprising any of iron powder, iron particulates, iron filings, iron shavings, and combinations thereof; contacting a mixture of the iron sample and the crude oil feedstock for a period of time at a sufficiently high temperature to react a portion of the iron sample with the naphthenic acid forming iron salts, and for at least a portion of the iron salts to decompose forming ketone; and measuring concentration of the ketone and iron salts in the mixture. The concentration of ketone can be measured by any of liquid chromatography, gas chromatography, mass spectrometry methods (GC-MS, ESI-MS, etc.), Fourier transform infrared spectroscopy (FT-IR), NMR, fractionation or transformation of the ketone to a chemical derivative for easier detection.

DETAILED DESCRIPTION

The following terms will be used throughout the specification and will have the following meanings unless otherwise indicated.

"Refinery feedstock" refers to natural and synthetic liquid hydrocarbon products including but not limited to crude oil, synthetic crude biodegraded oils, petroleum products, intermediate streams such as residue, naphtha, cracked stock; refined products including gasoline, other fuels, and solvents. The term "petroleum products" refer to crude oil, liquid, solid, and semi-solid hydrocarbon products including but not limited to tar sand, bitumen, etc. Refinery feedstock may be used interchangeably with crude or crude oil feedstock.

Crudes and crude blends are used interchangeably and each is intended to include both a single crude and blends of crudes.

The term naphthenic acid ("NA") refers to all of the organic acid content of a crude oil which become corrosive at higher temperatures, including but not limited to carboxylic acids, alkyl substituted acyclics (including fatty acids), aromatic acids, carbazoles, and isoprenoid acids. Examples include complex acid structures with two, three, and even four carboxylic groups (tetrameric acids) as well as structures containing heteroatoms.

The invention relates to methods for evaluating the corrosivity of refinery feedstocks, e.g., crude, particularly in the context of its naphthenic acid level.

Characterizing the Corrosion Mechanism: Typical high acid crude feedstocks contain naphthenic acids at levels that are corrosive to equipment in the process, with the following overall corrosion mechanism:

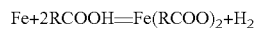

$$Fe + 2RCOOH = Fe(RCOO)_2 + H_2$$

Figure 1:
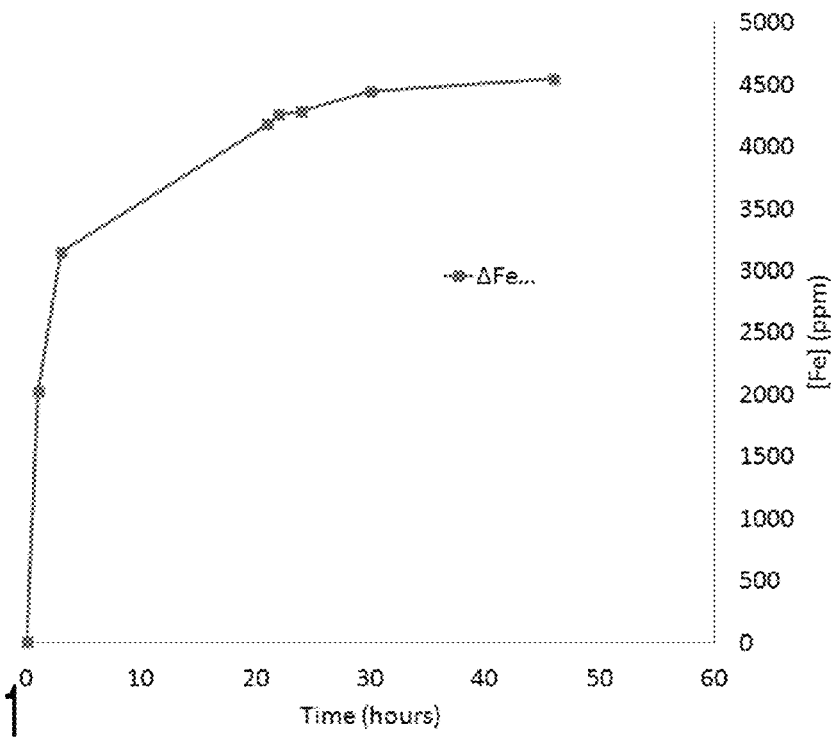
FIG. 1 is a graph showing the iron concentration as a function of time, after an iron sample is exposed to crude oil feedstock for an extended period of time at 260° C.
Figure 2:
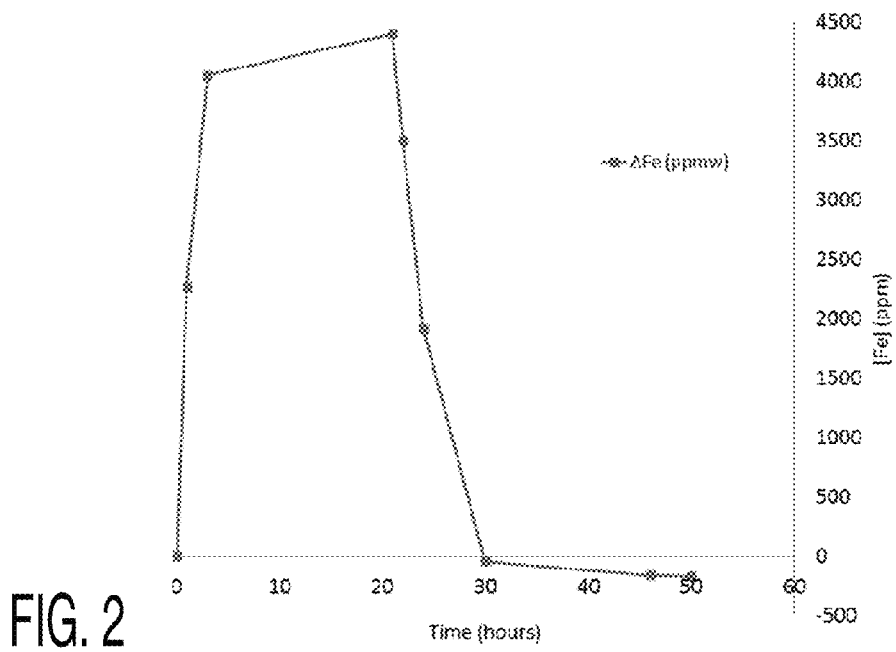
FIG. 2 is another graph showing change in the iron content in the feedstock as a function of time, as temperature increases from 260° C. to 343° C.

For corrosion detection due to the presence of naphthenic acid, the loss of reactants or the formation of products can be measured. The formation of products can be measured by either measuring the iron content in the oil or the hydrogen that evolves as illustrated in FIG. 1. However, the iron concentration (ppm) as a function of time (hours) as tested (in the form of iron powder) at a temperature of 270° C. shows a plateau in the concentration after an extended period of time. If the temperature is further increased to 343° C. (650° F.), a temperature that can be expected in the processing of crude feedstocks, the iron content quickly drops to zero as illustrated in FIG. 2. As shown, there is a rise in the iron content while heated at 260° C. (500° F.), and a drop to zero as temperature is ramped up at 20 hours, indicating a change in the chemical nature of the iron. Therefore, suggested methods in the art (e.g., Yepez et al in U.S. Pat. No. 6,294,387) for determining corrosiveness of naphthenic acid at a standard operating temperature of 270° C. or more would not work as there is no dissolved iron in the matrix to be measured.

Upon further analysis into the corrosion mechanism of iron due to the presence of naphthenic acid, e.g., the thermal decomposition of iron salt, it is stipulated that carboxylates salts decompose into ketones and iron oxides according to the reaction:

$$Fe(RCOO)_2 = CO_2 + FeO + RC=OR, \text{ where } RC=OR$$
is the ketone.

The above reaction would explain the absence of iron in the crude oil at a high operating temperatures, as the oxides would not be soluble and precipitate out of solution. There can be a slight variation of the oxide (FeO) formed by assuming both oxidation states of the iron salt are formed from the corrosion reaction:

$$Fe^{2+}(RCOO)_2 = CO_2 + FeO + RC=OR$$

$$2Fe^{3+}(RCOO)_3 = 3CO_2 + Fe_2O_3 + 3RC=OR$$

which yields the total reaction as:

$$Fe^{2+}(RCOO)_2 + 2Fe^{3+}(RCOO)_3 = 4CO_2 + FeO.Fe_2O_3 + 4RC=OR.$$

In one embodiment, the amount of magnetite formed can be employed as an indicator of the corrosivity of the crude oil feedstock. In another embodiment, the amount of ketone (i.e., the RC=OR species) is measured to quantify the corrosivity of a crude oil feedstock. The amount of iron lost is be calculated quantitatively in the full balanced reaction shown below, with the intermediate step shown in brackets:

$$8RCOOH + 3Fe = [4H_2 + Fe^{2+}salt + 2Fe^{3+}salt] = 4H_2 + 4CO_2 + FeO.Fe_2O_3 + 4RC=OR$$

As shown, four moles of ketone are produced from three moles of iron, thus quantifying the corrosivity of a crude oil feedstock over a period of time upon contact with equipment containing iron. Also in the reaction, carbon dioxide is shown to form, contradicting the common assumption that the sole source of $CO_2$ is from the decarboxylation of the parent acid.

Methods for Evaluating Corrosivity of Refinery Feedstocks:

Depending on the crude feedstock (as a stream or sample), some preparation of the crude may be needed. Preparation for sample analysis prior to characterization may include appropriate steps to remove particulate and/or solid matter, excess water, or other impurities. Excess water may be removed by a process of alternate heating and cooling of the sample, followed by centrifugation to remove the water. Alternatively, the water may be removed by separation. The heating process may be carried out in an inert atmosphere, e.g. under vacuum, nitrogen or helium or other inert gases.

In one embodiment, the crude feedstock is mixed with elemental iron ($Fe^\circ$) in the form of iron powder, iron particulates, iron filings, iron shavings, or combinations thereof, which would provide a high surface area for the reaction at expected operating temperatures or conditions for the corrosivity evaluation. In a second embodiment, other ferrous metallurgies such as steel, stainless steel, and higher alloys containing iron can be used. Collectively, these forms of iron or ferrous metallurgies are referred to as "iron sample." The iron sample has a surface area of at least 0.01 $m^2$/g in one embodiment; between 0.05-2 $m^2$/g in a second embodiment; between 0.2-1 $m^2$/g in a third embodiment; and at least 0.1 $m^2$/g in a fourth embodiment.

The iron sample is mixed into the crude oil feedstock in amounts sufficient to react with all of the naphthenic acid in the feedstock. Iron sample is added at a molar ratio of iron to naphthenic acid of at least about 1:2 in one embodiment; at least 20:1 in a second embodiment; at least 50:1 in a third embodiment; and at least 100:1 in a fourth embodiment. Iron sample is added to the crude feedstock at weight ratios ranging from 1:2 to 1:500 of iron sample to crude oil in one embodiment; 1:50 to 1:200 of iron to crude in a second embodiment; and at least 1:100 in a third embodiment. In another embodiment, iron sample is added to crude oil in a weight ratio of iron to naphthenic acid of 500:1 to 2:1.

In one embodiment, a vacuum is created while heating the crude feedstock to achieve vapor pressure at a given temperature, simulating vacuum distillation conditions. Under vacuum, the relative volatility of components increase, thus reducing the temperature required to bring acids and hydrocarbons to their boiling point. Because compounds are reactive at elevated temperatures, reducing the pressure and hence reducing the required temperature, certain degradation effects can be avoided while continuing to separate species by distillation when applied in the operating plant.

In one embodiment, the evaluation is carried out with the crude feedstock having different oxygen concentrations, e.g., from oxygen free oil (crude oil with an oxygen to content of less than 10 ppm) to oxygen having a much higher concentration of oxygen (e.g., to 500 ppm) to simulate different operating conditions. In another embodiment, the evaluation is carried out with crude oil feeds having different water and/or steam concentration to simulate the conditions existing in operations such as desalting, steam stripping. In one embodiment, the water level ranges from 10 ppm to 2%.

In one embodiment, the evaluation is carried out over a range of temperatures representative of the operation in a refinery, e.g., from ambient to 750° F., from 100° F. to 400° F., from 0° F. to 400° F., etc. The iron sample and the feedstock to be evaluated are mixed sufficiently to provide a substantially homogeneous mixture for at least fifteen minutes in one embodiment, at least 5 hours in a second embodiment, and at least 10 hours in a third embodiment.

After sufficient exposure to the crude oil feedstock and depending on the testing conditions, e.g., a temperature of about 250° C. or lower, a portion of the iron sample reacts with the feedstock and become dissolved (as $Fe^{+2}$) in the organic phase, and a remaining portion is present as a solid ($Fe^\circ$). In one embodiment, the portion dissolved into the organic phase is an iron carboxylate salt, e.g., iron naphthenate. Solids containing non-reacted iron and residues can be removed by means such as filtering the resulting mixed product. The dissolved iron concentration in the organic phase can be measured using conventional methods known in the art, including but not limited to inductively coupled plasma (ICP), infrared spectroscopy (FT-IR). Corrosivity can be derived from the concentration in terms of reaction rate units and/or [Fe] ppm/hr.

In one embodiment for corrosivity evaluation at severe operating conditions, e.g., at a temperature higher than about 260° C., a different and/or additional characterization step is carried out for a sufficient amount of time for at least a portion of the iron salts have decomposed into ketones and iron oxides. The reaction time is for at least 5 minutes in one embodiment; at least 15 minutes in a second embodiment; and at least 30 minutes in a third embodiment. At least a portion means at least 50% in one embodiment, at least 75% in a second embodiment, at least 90% in a third embodiment; at least 99% in a fourth embodiment; and all of the iron salts in a fifth embodiment. Solids containing non-reacted iron, iron oxides, etc., can be removed by means such as filtering the resulting mixed product, yielding an organic phase containing ketones.

In one embodiment, Fourier transform infrared spectroscopy (FT-IR) is employed as this analytical technique can differentiate between the iron salts, the ketone, as well as the parent acid inherently present in the crude oil feedstock. In another embodiment, any of known techniques including but not limited to elemental analysis, melting point, chemical degradation, gas or liquid chromatography, mass spectroscopy methods (GC-MS, ESI-MS, etc.), NMR, and fractionation or transformation of the ketone to a chemical derivative that is easier to detect can be employed to quantify and detect the presence of ketone in the organic phase. If any ketone is detected, corrosivity in terms of amount of iron reacted can be estimated from the ketone amount at the rate of 3 moles of iron producing 4 moles of ketone.

In one embodiment if magnetite can be recovered and separated from the unreacted iron sample for analysis by methods known in the art including but not limited to X-ray diffraction (XRD), the quantitative amount can be used as another way to evaluate the corrosivity of the crude feedstock.

Applications:

The method for evaluating the corrosivity of a crude based on its naphthenic acid level as quantified by the presence of ketone can be useful as a screening tool for oil and refinery fractions, new fields, refinery crude oil slates, and product streams. The method can also be used on current refinery and production operations to evaluate the impact of a crude feedstock on existing equipment.

The methods can also be used for defining and recommending blend ratios for optimal blends depending on the operating conditions and materials of construction of a particular refinery. There are a number of different parameters that can be used from the evaluation of the corrosivity based on ketone measurements, depending on the ultimate application, e.g., the refinery operating conditions, treatment plans for the crude, refinery equipment characteristics, etc. The refinery can determine the optimal dosage of chemical treatment and adjustment of performance parameters. The refinery can also assess the impact of cheaper crudes containing higher levels of naphthenic acid on existing equipment. Treatment plans as well as corresponding cost as such is known prior to using the crudes, allow for the risk assessment as well as advanced planning to mitigate any performance degradation due to the use of particular crudes or crude blends.

In one embodiment, the method is used to establish a reference database wherein corrosion data for referenced crude feedstocks containing known amounts of naphthenic acid is correlated to amounts of iron salts and/or ketones formed at different operating temperatures. The reference database can be used to characterize the corrosivity of a refinery feedstock, as well as in the optimization and blending of feedstock. For example, the ketone/iron salt measurements in a sample feedstock can be correlated to the data in the referenced database with corrosion rates to predict or anticipate the corrosion characteristics of the sample feedstock.

EXAMPLES

The following illustrative examples are intended to be non-limiting.

Example 1

The Example is to confirm the corrosion mechanism of crude oil containing naphthenic acid at a high temperature, e.g., the thermal decomposition of iron salt. 25 grams cyclohexane butyric acid is dissolved in 1800 mL of base oil and heated with 1018 carbon steel shavings at 343° C. (650° F.) for 24 hrs. The shavings are about 1/64" in diameter and about 1-2" long. Characterizing the oil after filtering by GC/MS confirms the presence of symmetric ketone. Further characterization of the ketone and carboxylic salt is done by FT-IR and ICP. The fine particles filtered from the oil are found to be magnetite ($FeO.Fe_2O_3$), confirmed by XRD.

Example 2

In this example, a sample of simulated crude oil feedstock is prepared. 70.5 grams of naphthenic acid is added to a beaker containing 1800 mL of base oil, and a sample is removed from analysis. Add 46 grams of steel shavings of approximately 1/64" in diameter and 1-2" long to an autoclave. Add simulated crude feedstock to the autoclave. Purge autoclave with nitrogen. Heat autoclave to 260° C. (500° F.). Ramp the temperature to 343° C. (650° F.) after 24 hours of testing has elapsed. Samples are removed from the autoclave for analysis prior to temperature ramp up, and periodically during the test. The examples are repeated with runs at 260° C. (500° F.) for 48 hours and at 343° C. (650° F.) for 48 hours.

GC/MS characterization conducted on the samples shows a peak near 22 minutes for the naphthenic acid. IR scans of the samples show the presence of the ketone (~sharp peak at 1715 $cm^{-1}$ for carbonyl C=O), iron salt (sharp peaks at ~1600 and 1400 $cm^{-1}$), and acid (sharp peak at 1700 $cm^{-1}$ and very broad peak at ~3400-2400 $cm^{-1}$ for —OH stretch).

For the purposes of this specification and appended claims, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present invention, inclusive of the stated value and has the meaning including the degree of error associated with measurement of the particular quantity.

It is noted that, as used in this specification and the appended claims, the singular forms "a," "an," and "the," include plural references unless expressly and unequivocally limited to one referent. As used herein, the term "include" and its grammatical variants are intended to be non-limiting, such that recitation of items in a list is not to the exclusion of other like items that can be substituted or added to the listed items.

As used herein, the use of "may" or "may be" indicates that a modified term is appropriate, capable, or suitable for an indicated capacity, function, or usage, while taking into account that in some circumstances the modified term may sometimes not be appropriate, capable, or suitable.

This written description uses examples to disclose the invention, including the best mode, and also to enable any person skilled in the art to make and use the invention. The patentable scope is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All citations referred herein are expressly incorporated by reference.

The invention claimed is:

1. A method for evaluating corrosivity of a crude feedstock, comprising:
providing a crude oil feedstock containing naphthenic acid;
providing an iron sample;

contacting a mixture of the iron sample and the crude oil feedstock for a period of time at a sufficiently high temperature to react a portion of the iron sample with the naphthenic acid; and measuring concentration of ketone in the mixture; and correlating the concentration of ketone to the corrosivity of the feedstock.

2. The method of claim 1, wherein the contacting is at a temperature of at least 260° C. for a portion of the iron sample to react with the naphthenic acid.

3. The method of claim 1, wherein the reaction between the iron sample with the naphthenic acid forms iron carboxylate salts.

4. The method of claim 3, further comprising measuring concentration of iron carboxylate salts in the mixture.

5. The method of claim 3, wherein at least a portion of the iron carboxylate salts decompose forming the ketone.

6. A method of claim 1, further comprising removing solids comprising non-reacted iron sample and iron oxides before the measuring step.

7. The method of claim 6, further comprising:
separating the non-reacted iron sample from the iron oxides; and
measuring concentration of the iron oxides.

8. The method of claim 1, wherein the concentration of ketone in the mixture is measured using any of gas chromatography, liquid chromatography, mass spectroscopy (MS), infrared spectroscopy (FT-IR), elemental analysis, fractionation, NMR, and combinations thereof.

9. The method of claim 1, wherein the iron sample is provided in an amount sufficient to react with all of the naphthenic acid in the crude oil feedstock.

10. The method of claim 1, wherein the iron sample is provided at a molar ratio of iron to naphthenic acid in the crude oil feedstock of at least about 1:2.

11. The method of claim 1, wherein the iron sample is provided at a weight ratio of iron to naphthenic acid in the crude oil feedstock of 500:1 to 2:1.

12. The method of claim 1, wherein the iron sample is provided at a weight ratio ranging from 1:2 to 1:500 of iron sample to crude oil feedstock.

13. The method of claim 1, wherein the iron sample is provided as any of iron powder, iron particulates, iron filings, iron shavings, and combinations thereof.

14. The method of claim 1, wherein the iron sample comprises any of steel, stainless steel, and higher alloys containing iron, and combinations thereof.

15. The method of claim 13, wherein the iron sample has a surface area of at least about 0.01 $m^2/g$.

16. The method of claim 1, wherein said contacting step is carried out under an inert atmosphere.

17. The method of claim 1, further comprising:
providing a reference database correlating ketone measurements with known naphthenic acid concentrations and corrosion performance of reference refinery feedstocks.

18. A method for evaluating corrosivity a crude feedstock, comprising:
providing a crude oil feedstock containing naphthenic acid;
providing an iron sample comprising any of iron powder, iron particulates, iron filings, iron shavings, and combinations thereof;
contacting a mixture of the iron sample and the crude oil feedstock for a period of time at a sufficiently high temperature to react a portion of the iron sample with the naphthenic acid forming iron salts, and for at least a portion of the iron salts to decompose forming ketone; and
measuring concentration of the ketone and iron salts in the mixture.

19. The method of claim 18, wherein the concentration of ketone in the mixture is measured using any of gas chromatography, liquid chromatography, mass spectroscopy (MS), infrared spectroscopy (FT-IR), elemental analysis, fractionation, NMR, and combinations thereof.

20. The method of claim 18, further comprising:
correlating the concentration of the ketone and the concentration of the iron salts with the corrosivity of the feedstock at a ratio of four moles of ketone to three moles of iron.

21. The method of claim 18, wherein the iron sample is provided in an amount sufficient to react with all of the naphthenic acid in the crude oil feedstock.

22. A method for optimizing blends of refinery feedstock, comprising:
providing a plurality of refinery feedstock samples containing naphthenic acid with each feedstock sample being representative of a feedstock stream to the refinery;
providing a plurality of iron samples;
contacting the refinery feedstock samples with the iron samples for a period of time at a sufficiently high temperature to react the iron samples with the naphthenic acid in the refinery feedstock samples;
measuring concentration of ketone in each mixture of refinery feedstock and iron sample;
providing a reference database correlating ketone measurements with known naphthenic acid concentrations and corrosion performance of reference refinery feedstocks;
using the ketone measurements of the refinery feedstock samples and the reference database correlating ketone measurements with known naphthenic acid concentrations and corrosion performance to obtain a feedstock blend having acceptable corrosion performance.

23. The method of claim 22, further comprising measuring concentration of iron carboxylate salts in each mixture of refinery feedstock and iron sample.

* * * * *